United States Patent
Syage et al.

(10) Patent No.: US 8,402,842 B2
(45) Date of Patent: Mar. 26, 2013

(54) SURFACE SAMPLING MOBILE CHEMICAL DETECTION PROBE

(75) Inventors: Jack A. Syage, Huntington Beach, CA (US); Paul T. Chaney, La Habra, CA (US)

(73) Assignee: Morpho Detection, Inc, Newark, CA (US)

( * ) Notice: Subject to any disclaimer, the term of this patent is extended or adjusted under 35 U.S.C. 154(b) by 560 days.

(21) Appl. No.: 12/650,195

(22) Filed: Dec. 30, 2009

(65) Prior Publication Data

US 2011/0154918 A1 Jun. 30, 2011

(51) Int. Cl.
*G01N 1/14* (2006.01)

(52) U.S. Cl. ........... 73/863.23; 73/863.11; 73/864.35

(58) Field of Classification Search .......... 73/863.12, 73/863.23, 864.35
See application file for complete search history.

(56) References Cited

U.S. PATENT DOCUMENTS

| | | |
|---|---|---|
| 4,541,268 A | 9/1985 | Odernheimer |
| 4,982,616 A | 1/1991 | Koch et al. |
| 5,113,711 A | 5/1992 | Davloor et al. |
| 5,318,911 A | 6/1994 | Fine et al. |
| 5,517,026 A | 5/1996 | Sickenberger et al. |
| 5,551,278 A * | 9/1996 | Rounbehler et al. ........... 73/1.06 |
| 5,843,379 A | 12/1998 | Kristensen |
| 5,859,362 A | 1/1999 | Neudorfl et al. |
| 5,950,642 A | 9/1999 | Auck et al. |
| 5,988,002 A | 11/1999 | Danylewych-May et al. |
| 6,477,907 B1 | 11/2002 | Chambers et al. |
| 6,817,225 B2 | 11/2004 | Boyd et al. |
| 7,073,403 B2 | 7/2006 | Albro et al. |
| 7,281,439 B2 | 10/2007 | Schmitt et al. |
| 7,357,044 B2 | 4/2008 | Sleeman et al. |
| 7,579,587 B2 | 8/2009 | Krough et al. |
| 2011/0044853 A1 * | 2/2011 | Devine ........................ 422/33 |

* cited by examiner

*Primary Examiner* — Hezron E Williams
*Assistant Examiner* — Paul West
(74) *Attorney, Agent, or Firm* — Armstrong Teasdale LLP (57) ABSTRACT

A sampling device that contains a heated porous inlet and a transfer line. The device provides sample compounds present as vapor, liquid, or solid, in air, or on surfaces such as soil. The sample device can collect and deliver the sample to an analyzer in real time and can operate while in motion such as on a moving vehicle. The sampling device is especially useful to screen toxic and hazardous compounds that might be contaminating an inhabited area.

19 Claims, 9 Drawing Sheets

SURFACE SAMPLING MOBILE CHEMICAL DETECTION PROBE

BACKGROUND OF THE INVENTION

1. Field of the Invention

The present invention relates to a device for collecting solid, liquid, and vapor sample from surfaces.

2. Background Information

One of the most challenging parts of an effective chemical detection system is the means of collecting and delivering sample to the detector. There have been developed a wide variety of chemical detection applications for chemical sample types. These applications range from volatile to solid compounds that may be found in a host of different media ranging from air, to water, to solid surfaces such as soil. The additional requirements of real-time detection and use in mobile applications adds to the challenge. Many detection technologies (e.g., mass spectrometry, ion mobility spectrometry, optical spectroscopy, etc.) have been developed over the years and trace detectors now exist that can detect a wide range of chemicals. Whereas the specificity of a detector is the key to minimizing false positive rates, the sampler is vital for maximizing detection rates, since if a trace sample is not delivered to the detector, it will result in a non-detect event.

An effective sampling system must have the following operational characteristics: (1) access to the surface and volume containing the contamination, (2) removal of the contamination, particularly for liquids and solids that can stick tightly to surfaces, (3) delivery of the material to a trace detector in a step that involves vaporization, and (4) minimizing cycle time and carryover effects. For trace chemical analyzers, the liquid and solid sample must be vaporized. There are a large number of published and patented chemical sampling devices that deal with some part of the applications described above, but none accomplish all of the requirements.

U.S. Pat. No. 4,541,268 issued to Odernheimer discloses a collector surface that is brought into contact with material to be sampled and then transferred to a membrane that is heated for delivery to a detector. The membrane is based on selective permeation and therefore has the function of enriching compounds, but in fact this is achieved through selectivity, which is molecule dependent, and is therefore prone to selectively suppress some compounds. Furthermore, a permeation membrane reduces the response time and recovery of the sampler. Several samplers use membranes as the interface between the sample and the detector including U.S. Pat. No. 5,517,206 issued to Sickenberger, et al. and U.S. Pat. No. 5,843,379 issued to Kristensen.

U.S. Pat. No. 6,817,225 issued to Boyd, et al. disclosed a volatile organic compound (VOC) sampling probe that is partially buried in the ground. U.S. Pat. No. 7,281,439 issued to Albro, et al. also discloses a VOC sampler for subsurface soil analysis. However, neither of these devices allow mobile use, nor do they sample liquid or solid samples effectively. U.S. Pat. No. 7,357,044 issued to Sleeman, et al. discloses a movable sample collection and desorption device, but it does not allow vapor and condensed compound detection, nor does it allow for sampling in dirty environments such as soil.

BRIEF SUMMARY OF THE INVENTION

A sampler that collects and transfers a sample to a detector. The sampler includes a housing that has a transfer line, and a porous frit attached to the housing. The porous frit has an exposed outer surface and is in fluid communication with the transfer line. The sampler also has a heater coupled to the housing.

DETAILED DESCRIPTION

Disclosed is a sampling device that contains a heated porous inlet and a transfer line. The device provides sample compounds present as vapor, liquid, or solid, in air, or on surfaces such as soil. The sample device can collect and deliver the sample to an analyzer in real time and can operate while in motion such as on a moving vehicle. The sampling device is especially useful to screen toxic and hazardous compounds that might be contaminating an inhabited area.

What is describe is a technology for sampling vapor in air and liquid and solid samples from surfaces for analysis using a chemical analyzer such as a mass spectrometer. Furthermore this technology is capable of operating in a mobile vehicle and providing real-time sample collection and delivery. A particular, but not limiting application, is the screening for the presence of toxic chemicals, such as chemical warfare agents and toxic industrial compounds, on the ground and in the surrounding air. The sampling probe is preferably consistent with detection by personnel in safe environment, such as in an enclosed vehicle.

The chemical sampling probe and delivery system can sample vapor, liquid, and solid samples in air and on surfaces and do so at high rates of speed in hazardous environments. The device uses a heated porous metal inlet that can contact condensed sample and cause vaporization that is drawn through the porous inlet. The inlet pore size is sufficiently small to prevent particulate from entering. The porous inlet enables high flow rates permitting real-time analysis and also is not selective in what passes through unlike membrane inlets. In one embodiment the probe head also has air jets enabling agitation of the surface to draw material into contact with the porous metal inlet without the inlet making direct contact with the surface being sampled. Various other embodiments are disclosed enabling the device to be operated on a fast moving vehicle in a dirty environment.

Figure 1A:
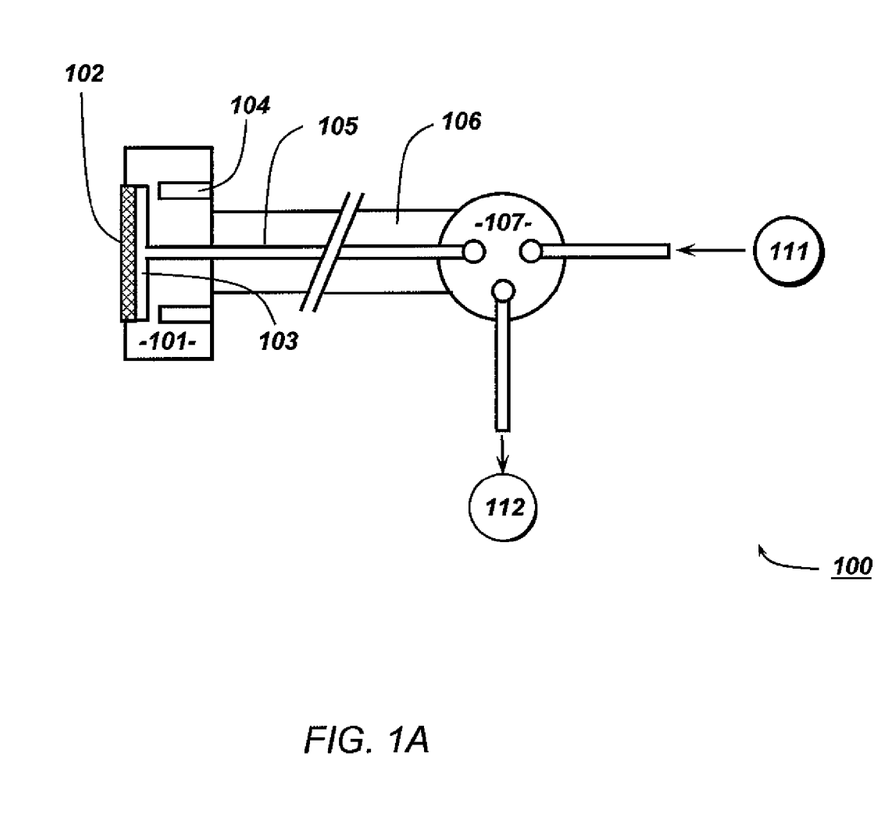
FIGS. 1A and 1B are illustrations that show a sampling device consisting of a heated porous inlet and a narrow transfer channel.
Figure 1B:
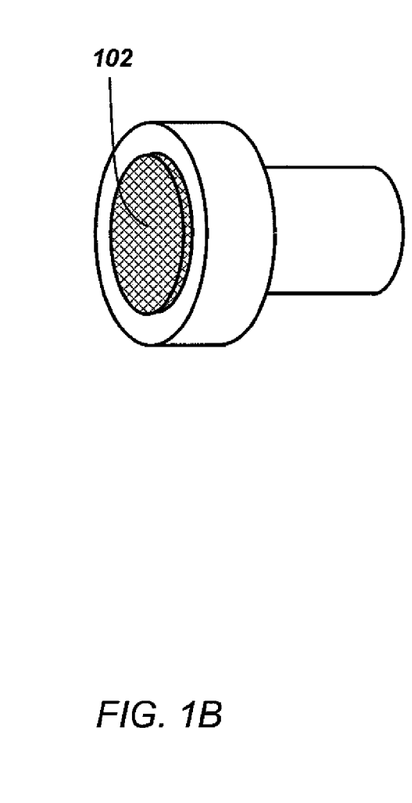

Referring to the drawings more particularly by reference numbers, FIGS. 1A and 1B show an embodiment of a sampling device 100. The device has a sampling probe 101 consisting of a porous filter 102, such as a metal mesh, heaters 104, a low volume channel 103, a transfer channel or capillary 105, and a housing 106 containing the transfer channel to provide heating and flexible movement. The sampling device also may contain a valve 107 to allow sample to be pulled by a pump or vacuum 112. The pump or vacuum 112 may be connected to a chemical analyzer and the chemical analyzer may also provide the pump or vacuum to draw the sample. A backpressure may also be applied to the transfer line through pump 111 and valve 106 in order to clear out sample and also to purge the porous filter 102.

The porous filter 102 has the property that the pores are sufficiently small to prevent particulate matter from penetrating and entering the transfer line 105. Typically, transfer line inner diameters can range from one micron to 500 microns (0.5 mm). It is desirable then to have a porous filter 102 with pores smaller than the appropriate diameter. Even for larger transfer line diameters is it desirable to have small pore sizes to keep particulate from entering into the transfer line and then entering into a detector or other device. By way of example, the porous filter can be a porous metal frit. Such frits are available for example with typical pore sizes of 2 microns and with sufficient pore density to provide a maximum flow of air, although it is to be understood that the frits may have larger pore sizes. The porous filter 102 may also be heated so that liquid and solid compounds will vaporize and only the vapor penetrates the filter. The probe head 101 and the transfer line housing 106 are heated to maintain the sample in vapor form. The porous filter 102 is to be contrasted with membranes of the prior art. Membranes have pore sizes much smaller than 1 micron in order to impede air flow and instead uses the property of selective binding to pass certain compounds. This has the effect of concentrating certain compounds, but also can discriminate against other compounds. The porous frit on the other hand does not impede the flow of air and does not use selective binding for certain compounds. Instead the entire sample contained in air passes through the porous frit, yet particulate and other matter is stopped by the pore size.

Figure 2A:
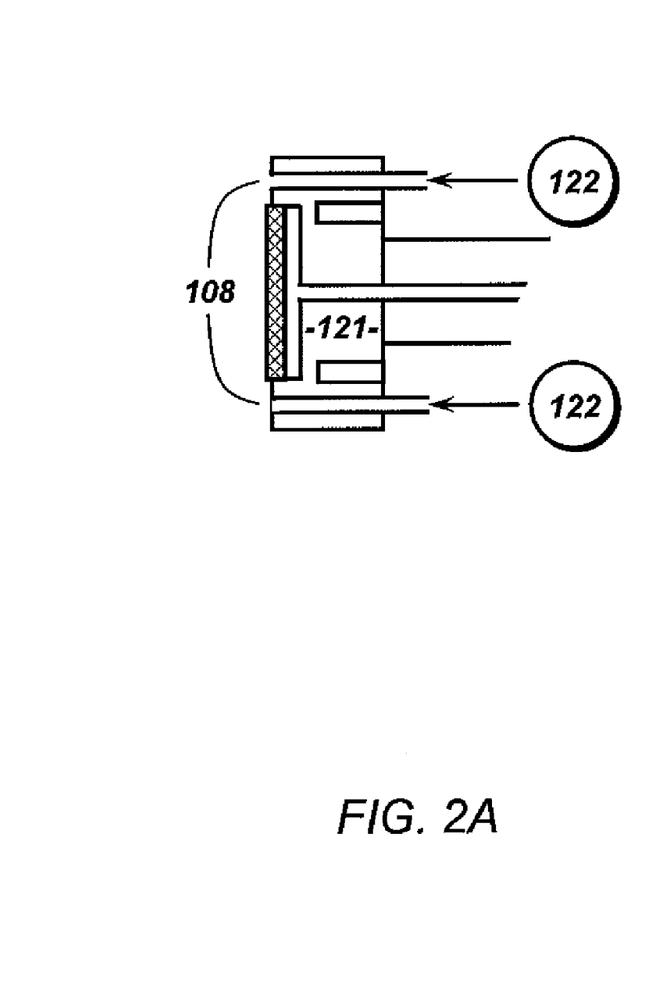
FIGS. 2A and 2B are illustrations of a sampling device that includes air jets.
Figure 2B:
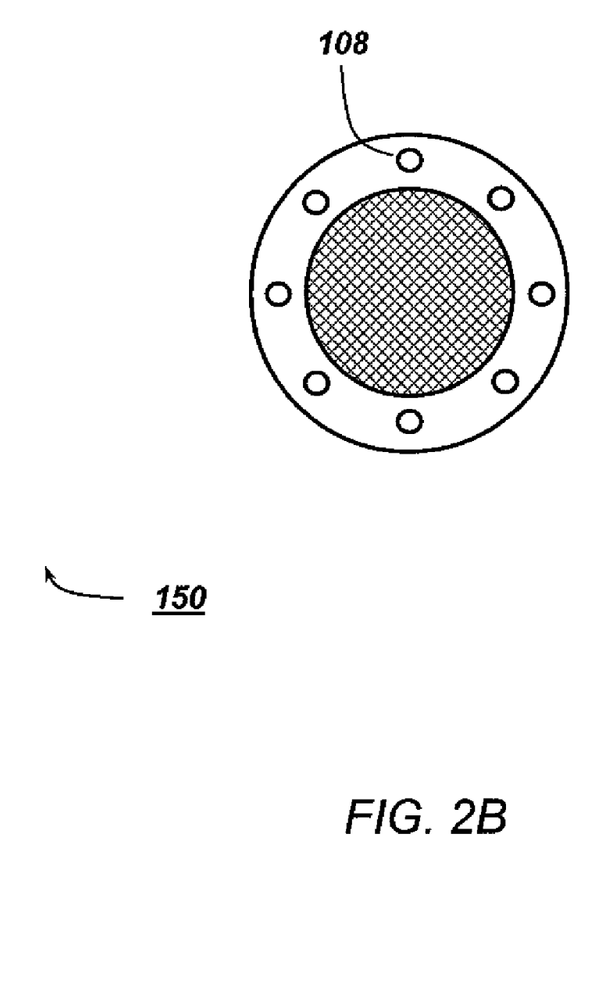

FIGS. 2A and 2B show an embodiment of the sampling device 150 that has air jets 108 in the probe head 121 to agitate the sample surface to help loosen sample from the surface. The air jets 108 are pressurized by a pump 122. Another purpose of the air jets is to allow the sample on the surface to be driven toward the porous filter inlet 102 so that the inlet does not actually have to make contact with the surface. This is an important property if the sampling device is in motion relative to the surface. By way of example it may be desirable to sample the outdoor ground from a moving vehicle. The use of air jets can stir up the ground. If the ground consists mostly of soil and/or vegetation, this material can be driven off the ground and made to contact the inlet 102. If liquid or solid chemical material is present, then it will come into contact with the heated inlet 102 and vaporize. These vapors are then drawn through the inlet filter 102 and into the transfer line 105 by the pumping action of pump 112. It is important to realize that the sampling device 100 also serves as a vapor collection system. If chemicals exist as vapor in the air, it will be drawn into the inlet 102 and transfer line 105.

Figure 3:
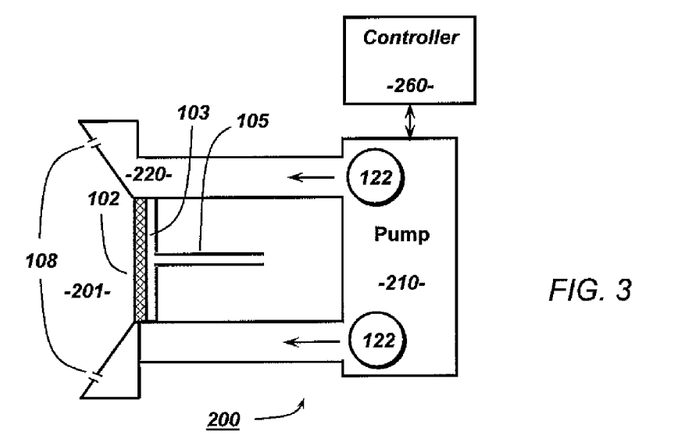
FIG. 3 is an illustration of an embodiment of a sampling device with air jets arranged in a nozzle.
Figure 4:
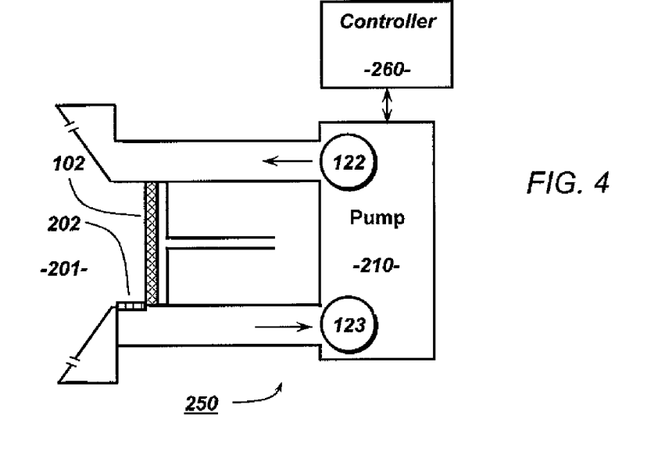
FIG. 4 is an illustration of an embodiment of a sampling device with air jets arranged in a nozzle and with an intake airflow.

FIGS. 3 and 4 show embodiments of the sampling device with air jets configured with a sampling nozzle. In FIG. 3 the sampling device 200 has a nozzle with air jets 108 that are slanted toward the centerline of the sampling probe 220. This causes agitation of the surface and a sampling volume 201 is then drawn toward the inlet 102. The sampling device has a pump 210 that provides pumping flow 122. The pump 210 can be controlled by a controller 260 to turn the air jet flow on and off and provide either continuous or pulsed application of air jets. FIG. 4 shows an embodiment of a sampling device 250 in which the pump 210 provides both an overpressure 122 and an underpressure 123. The underpressure 123 can be used to help assist the flow of sample volume 201 toward the inlet 102.

Figure 5A:
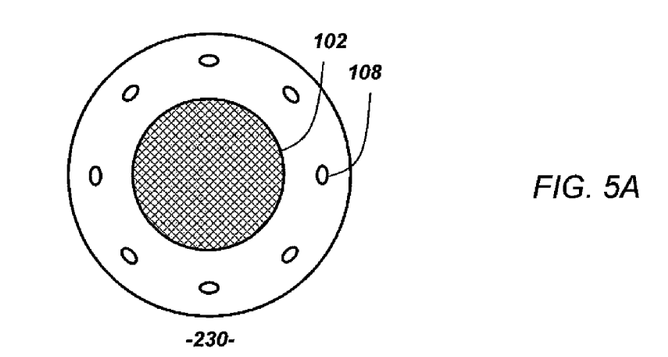
FIGS. 5A-C are illustrations showing different arrangements of the air jets about an inlet.
Figure 5B:
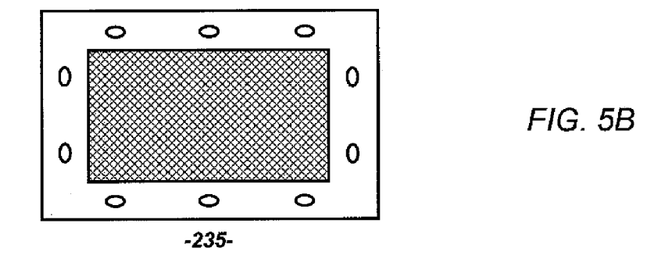
Figure 5C:
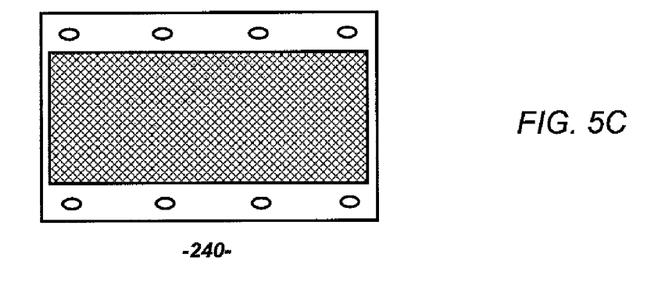

FIGS. 5A-C show different configurations for the nozzle containing air jets 108 and inlet filter 102. The nozzle 230 has a circular configuration and the nozzle 235 has a rectangular configuration. Nozzle 240 also has a rectangular configuration, but the air jets are on only two sides. Other configurations may also be used.

An important utility of the disclosed invention is the capability to collect sample from a surface while the sampling device is in motion. The sampling devices in FIGS. 3 and 4 can be moved across a surface either manually or automatically. In the automatic mode, the air jets can be used to apply pressure to the surface to prevent the sampling device from making direct contact with the surface or at least not making hard contact with the surface.

Figure 6:
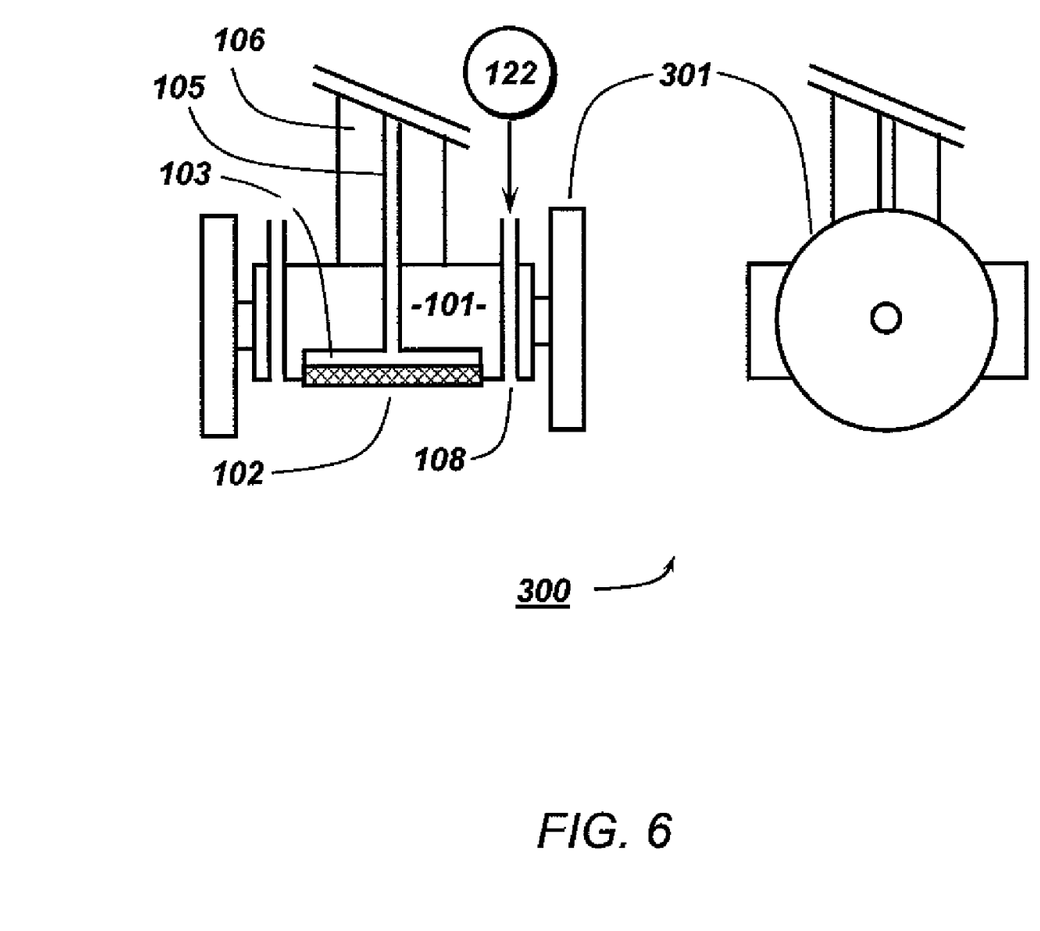
FIG. 6 is an illustration of an embodiment of a sampling device with wheels or standoffs to keep the inlet from touching the sampled surface.

FIG. 6 shows an embodiment of a sampling device 300 in which the sampling probe 101 has wheels 301 that roll along the surface to keep the inlet filter 102 at a reasonably fixed distance from the surface. It is not necessary that the wheels 301 rotate. They may also be sliding devices. The probe head 101 may have air jets 108 pressurized by a pump 122 to agitate the surface and drive sample and surface material to the inlet 102. As described above the surface material and any liquid or solid compounds would vaporize on the heated inlet surface and be drawn into the transfer line 105.

Figures 7A, 7B:
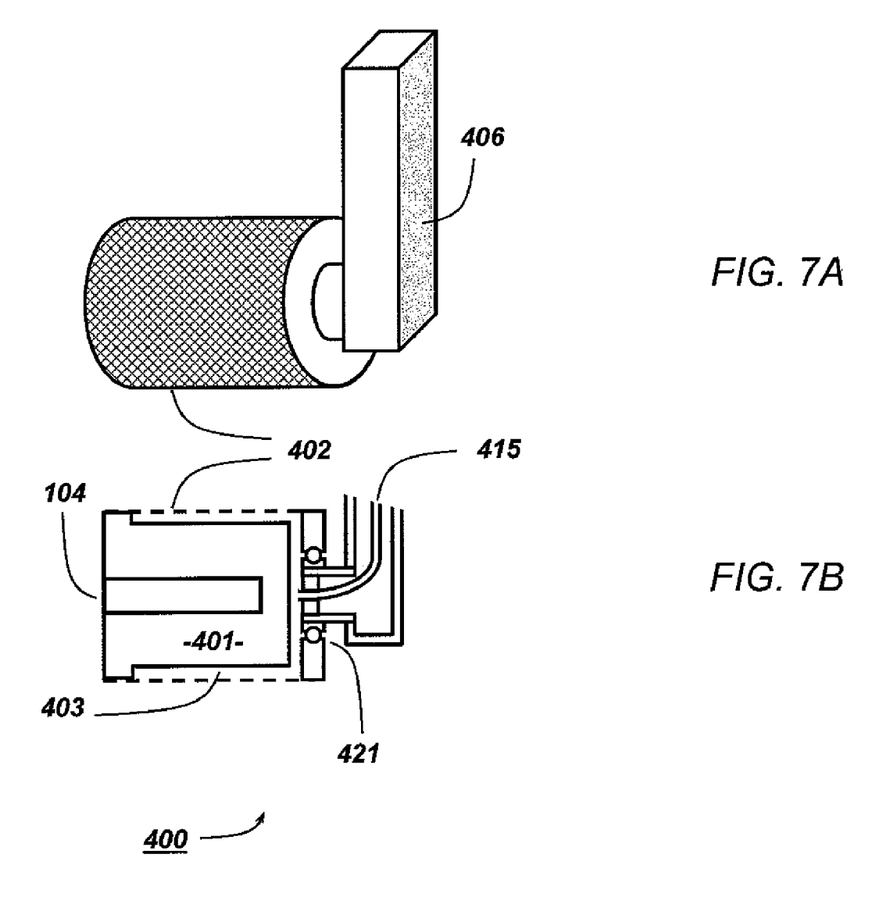
FIGS. 7A-B are illustrations of an embodiment of a sampling inlet consisting of a rotating, or non-rotating, cylinder.

FIGS. 7A and 7B, and 8A and 8B, show embodiments of a sampling device that can screen for sample on surfaces while in motion and while making direct contact with the surface. FIGS. 7A and 7B show a sampling device 400 in which the probe head 401 consists of a cylindrical inlet filter 402. The volume inside the inlet filter 403 is minimized by the shape of the probe head internal block 401. Minimizing internal volumes reduces the sample transfer time and allows sample to reach an analyzer in real time. A heater 104 may also be used to provide heat to assist in the vaporization of liquid and solid chemical sample. The cylindrical inlet filter 402 and probe head 401 may rotate about the transfer line 415 relative to housing 406. This rotation can be achieved using a ball bearing or similar interface 421.

Figure 8A:
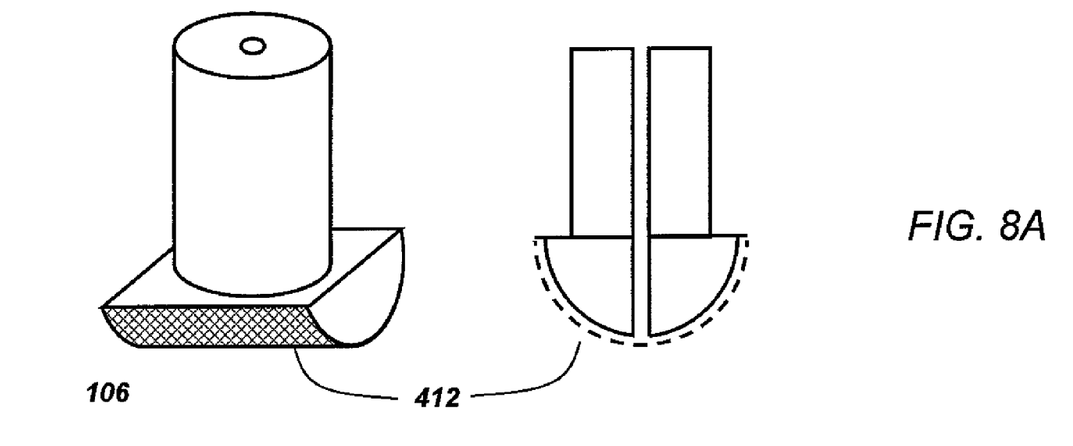
FIGS. 8A-B are illustrations of an embodiment of a sampling inlet that has a curved surface.
Figure 8B:
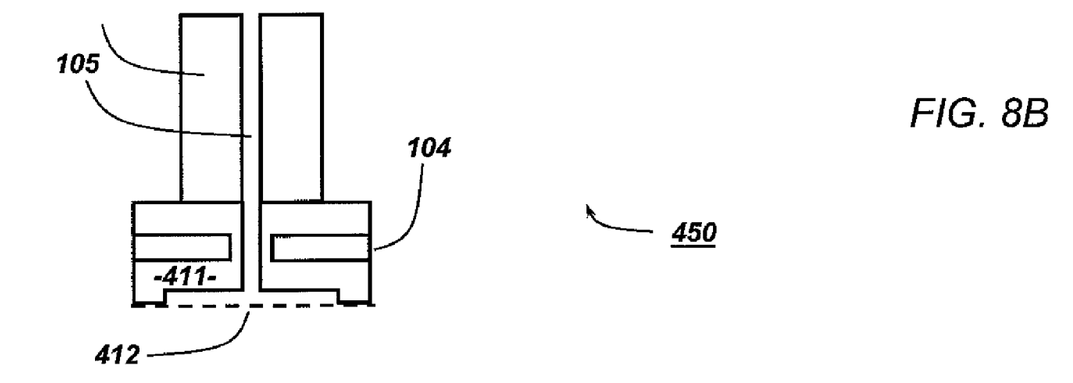

The sampling device 400 shown in FIGS. 8A and 8B may be operated without rotation if desired, and shows another embodiment of the sampling device 450 that enables direct contact with a surface while the sample device is in motion. The probe head 411 is in the form of a half cylinder and consists of an inlet filter 412 along the curved surface. This shape may be dragged across the surface to be sampled.

Figure 9:
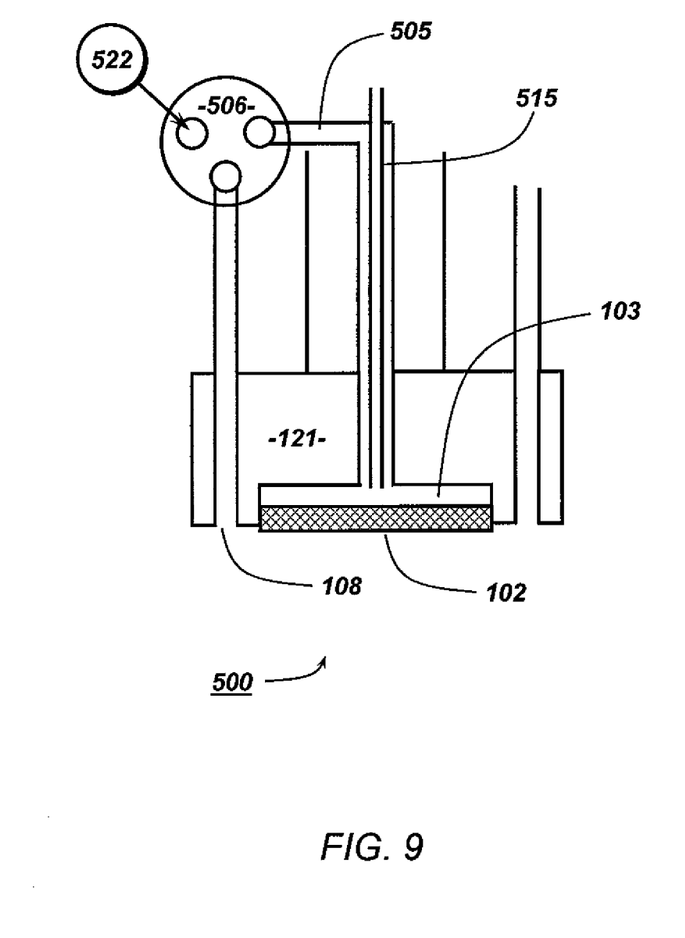
FIG. 9 is an illustration of an embodiment of a sampling inlet that has means to provide a backpressure to the inlet.

The invention disclosed here is intended for sampling off of surfaces including very dirty surfaces in hostile environments. By allowing the porous inlet filters to be exposed to a variety of materials, such as soil, there is a potential for the filter to become dirty and begin to clog. FIGS. 1A and 1B show a method that was described above for providing a backpressure through the transfer line 105 that can then pass through the inlet filter 102 to clear any debris in the filter pores. FIG. 9 discloses another method for providing a backpressure to the inlet 102. The transfer line 515 in sampling device 500 can be the source of the overpressure, but the total pressure may be limited by the small internal diameter of the transfer line 515. An alternative is to use a larger size channel 505 for the overpressure. This would allow higher backpressure to be applied to the inlet filter 102 creating a more effective means to blow out any material that may be impeding the flow of sample into the filter 102. FIG. 9 also shows that the source of the overpressure may be the same pumping source 522 used to provide overpressure to the air jets 108. In this case sample device 500 may include a valve 506 that can switch the air jet overpressure to the inlet filter 102 by way of channel 505.

An important attribute of the sample devices disclosed in this invention is the capability to sample and analyze chemicals in the air and on surfaces in real time. This capability requires designing a sample device that has minimal internal volume and sufficient volume air flow. The use of a membrane interface, such as what has been employed for previous sampling devices causes a slow response time due to the permeation rate of compounds through a membrane. The present invention uses a porous filter that does not impede the flow of vapor sample, but does prevent the flow of particulate matter. The main time limiting component of the present invention for the analysis of chemical samples is the sample conductance through the transfer line 102. To understand the transit time and time response for the transfer line we refer to the Poiseuille equation for the throughput U through a straight tube for viscous flow, as would occur at atmospheric pressure. The throughput for air sample in units of volume pressure per unit time is given by $$U = \frac{\pi d^4}{256 \eta L} \frac{(P_1 + P_2)}{2} (P_1 - P_2)$$

where $P_1$ is the inlet pressure, $P_2$ is the vacuum pressure 112 drawing air through the transfer line 105, d and L are the internal diameter and length of the transfer line 105, and $\eta$ is the viscosity of air which is 184 g cm$^{-1}$s$^{-1}$. For an inlet at 1 atmosphere of pressure that expands into vacuum $P_1 \gg P_2$ and atmospheric pressure equals $1.01 \times 10^6$ g cm$^{-1}$s$^{-1}$.

Figure 10:
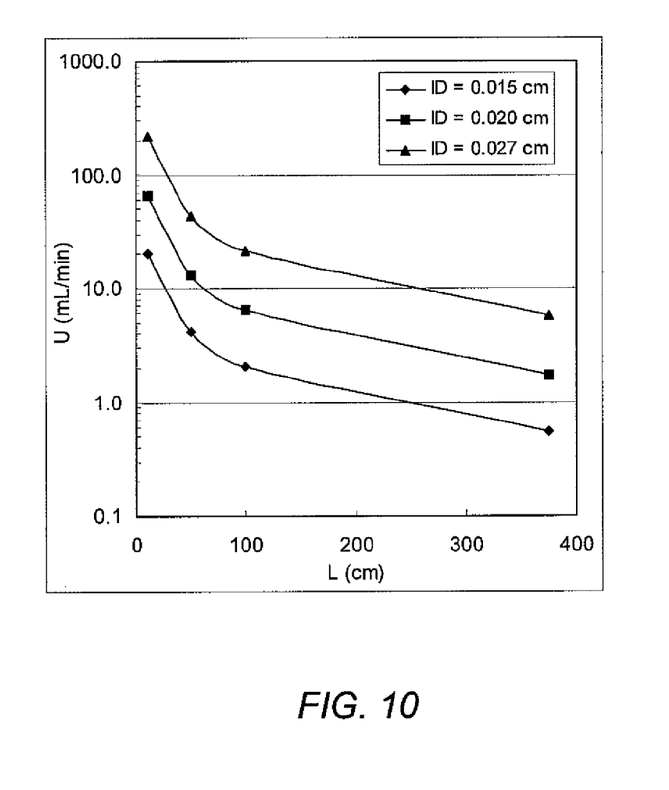
FIG. 10 is a graph that shows plots of the sampling gas throughput U versus transfer line inner diameter ID and length L; and, FIG. 11 is a graph that shows plots of the transfer time of sample through the transfer line versus transfer line inner diameter ID and length L.
Figure 11:
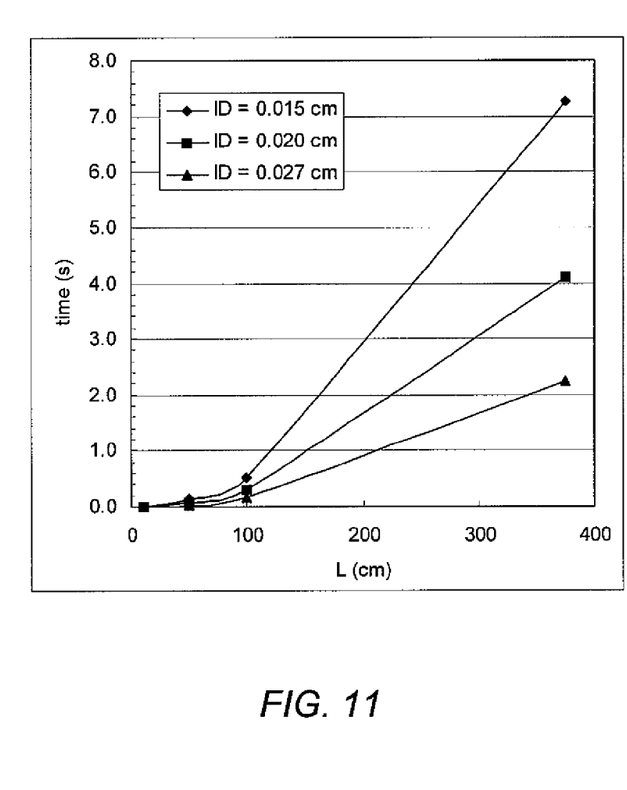

The tables below show the throughput U and transit time as a function of the transfer line internal diameter d and length L. These values are also plotted in FIG. 10. Based on these calculations and borne out by laboratory measurements, it is possible to achieve transit times on the order of 2 s for sample device lengths up to 3.75 m and a throughput of about 6 mL/min. The latter throughput is consistent with many mass spectrometer analyzers.

| | | Throughput (mL/min) | | | |
|---|---|---|---|---|---|
| d(cm) | L(cm) | 10 | 50 | 100 | 375 |
| 0.015 | | 20.52 | 4.10 | 2.05 | 0.55 |
| 0.020 | | 64.84 | 12.97 | 6.48 | 1.73 |
| 0.027 | | 215.37 | 43.07 | 21.54 | 5.74 |

| | | Transit time (s) | | | |
|---|---|---|---|---|---|
| d(cm) | L(cm) | 10 | 50 | 100 | 375 |
| 0.015 | | 0.01 | 0.13 | 0.52 | 7.27 |
| 0.020 | | 0.00 | 0.07 | 0.29 | 4.09 |
| 0.027 | | 0.00 | 0.04 | 0.16 | 2.24 |

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

The invention claimed is:

1. A sampler that collects and transfers a sample to a detector, comprising:
    a housing that includes a transfer line;
    a porous frit attached to said housing, said porous frit has an exposed outer surface and is in fluid communication with said transfer line;
    at least one pump;
    a plurality of air jets coupled to said at least one pump, wherein said plurality of air jets are configured to induce a negative pressure; and,
    a heater coupled to said housing.

2. The sampler of claim 1, wherein said at least one pump comprises a first pump in fluid communication with said transfer line.

3. The sampler of claim 2, further comprising a second pump and a valve that can couple said first or second pump to said transfer line, said first pump creates a negative pressure and said second pump creates a positive pressure within said transfer line.

4. The sampler of claim 1, further comprising a probe head that includes said air jets.

5. The sampler of claim 1, further comprising a controller coupled to said at least one pump to provide either a continuous overpressure or a pulse overpressure within said transfer line.

6. The sampler of claim 1, wherein said housing includes an offset structure that elevates said porous frit from a surface.

7. The sampler of claim 1, wherein said outer surface of said porous frit has a radial shape.

8. The sampler of claim 1, wherein said housing can rotate about an axis.

9. The sampler of claim 1, wherein said housing has an overpressure channel.

10. The sampler of claim 9, further comprising a valve configured to switch said at least one pump to be in fluid communication with either said transfer line or said overpressure channel.

11. The sampler of claim 1, wherein said porous frit has a pore size that ranges from about 1 to 500 microns.

12. A method for collecting and transferring a sample to a detector, comprising:
    energizing at least one pump;
    inducing a negative pressure in a plurality of air jets coupled in flow communication with the at least one pump;
    pulling a sample from a surface into a porous frit that is attached to a housing;
    heating the sample; and,
    transferring the heated sample through a transfer line of the housing to a detector.

13. The method of claim 12, wherein the porous frit is separated from the surface, wherein the surface includes at least one of outside ground surfaces, soil surfaces, and curved surfaces.

14. The method of claim 12, wherein the porous frit is in contact with the surface, wherein the surface includes at least one of outside ground surfaces, soil surfaces, and curved surfaces.

15. The method of claim 12, further comprising moving the porous frit relative to the surface, wherein the surface includes at least one of outside ground surfaces, soil surfaces, and curved surfaces.

16. The method of claim 12, further comprising purging the porous frit with an overpressure within the transfer line.

17. The method of claim 16, further comprising switching a valve to change a pressure within the transfer line from a negative pressure to a positive pressure.

18. The method of claim 12, further comprising agitating the surface with an air jet emitted by the housing.

19. The method of claim 18, wherein the air jet is either continuous or pulsed.

* * * * *